US010081910B2

(12) United States Patent
Barrera et al.

(10) Patent No.: US 10,081,910 B2
(45) Date of Patent: Sep. 25, 2018

(54) ABSORBENT ARTICLES COMPRISING ORGANOPOLYSILOXANE CONDITIONING POLYMERS

(71) Applicant: The Procter & Gamble Company, Cincinnati, OH (US)

(72) Inventors: Carola Barrera, West Chester, OH (US); Steven Daryl Smith, Fairfield, OH (US); Robert Joseph McChain, Cincinnati, OH (US); Yonas Gizaw, West Chester, OH (US); Rajan Keshav Panandiker, West Chester, OH (US); Charles William Neal, Fairfield, OH (US); John Lee Hammons, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 757 days.

(21) Appl. No.: 14/604,782

(22) Filed: Jan. 26, 2015

(65) Prior Publication Data

US 2015/0147568 A1    May 28, 2015

Related U.S. Application Data

(63) Continuation of application No. PCT/US2013/052594, filed on Jul. 29, 2013.

(51) Int. Cl.
| | |
|---|---|
| *D06M 15/643* | (2006.01) |
| *C09D 183/06* | (2006.01) |
| *A61L 15/22* | (2006.01) |
| *A61F 13/15* | (2006.01) |
| *D21H 27/02* | (2006.01) |
| *D21H 27/00* | (2006.01) |
| *C08G 77/388* | (2006.01) |
| *C08G 77/452* | (2006.01) |
| *C08L 83/10* | (2006.01) |
| *A61F 13/511* | (2006.01) |
| *C08G 77/00* | (2006.01) |

(52) U.S. Cl.
CPC ... *D06M 15/6436* (2013.01); *A61F 13/15203* (2013.01); *A61F 13/51113* (2013.01); *A61L 15/225* (2013.01); *C08G 77/388* (2013.01); *C08G 77/452* (2013.01); *C08L 83/10* (2013.01); *C09D 183/06* (2013.01); *D21H 27/002* (2013.01); *D21H 27/02* (2013.01); *B32B 2555/02* (2013.01); *C08G 77/70* (2013.01); *D06M 2200/50* (2013.01); *Y10T 428/273* (2015.01); *Y10T 442/2352* (2015.04)

(58) Field of Classification Search
CPC .. C08G 77/26; C08G 77/452; D06M 15/6436
USPC ............. 252/8.61–8.63; 528/28, 38
See application file for complete search history.

(56) References Cited

U.S. PATENT DOCUMENTS

| | | | |
|---|---|---|---|
| 3,560,543 | A | 2/1971 | Plueddemann |
| 4,200,724 | A | 4/1980 | Darms et al. |
| 4,293,397 | A | 10/1981 | Sato |
| 4,533,714 | A | 8/1985 | Sebag et al. |
| 4,833,225 | A | 5/1989 | Schaefer et al. |
| 5,300,167 | A | 4/1994 | Nohr et al. |
| 5,358,667 | A | 10/1994 | Bergmann |
| 5,476,660 | A | 12/1995 | Somasundaran |
| 5,659,001 | A | 8/1997 | De La Croi Habimana et al. |
| 5,925,341 | A | 7/1999 | Cervantes et al. |
| 6,093,240 | A | 7/2000 | Matsumura et al. |
| 6,201,058 | B1 | 3/2001 | Mahr et al. |
| 6,338,855 | B1 | 1/2002 | Albacarys |
| 6,395,858 | B1 | 5/2002 | Mack et al. |
| 6,491,838 | B1 | 12/2002 | Standke et al. |
| 6,515,095 | B1 † | 2/2003 | Omura |
| 6,641,870 | B2 | 11/2003 | Bartkowiak et al. |
| 6,833,344 | B2 | 12/2004 | Boutique |
| 6,878,770 | B2 | 4/2005 | Herzig |
| 6,903,061 | B2 | 6/2005 | Masschelein |
| 7,118,057 | B2 | 10/2006 | Hao |
| 7,217,777 | B2 | 5/2007 | Lange et al. |
| 7,294,612 | B2 | 11/2007 | Popplewell et al. |
| 7,514,091 | B2 | 4/2009 | Restle et al. |
| 7,563,856 | B2 | 7/2009 | Lange |
| 7,563,857 | B2 | 7/2009 | Lange |
| 7,871,972 | B2 | 1/2011 | Sengupta |
| 7,888,306 | B2 | 2/2011 | Sengupta |
| 8,158,572 | B2 | 4/2012 | Schubert |
| 8,367,791 | B2 | 2/2013 | Byrd et al. |
| 8,440,174 | B2 | 5/2013 | Panandiker |
| 2003/0147842 | A1 | 8/2003 | Restle et al. |

(Continued)

FOREIGN PATENT DOCUMENTS

| | | |
|---|---|---|
| CN | 101956324 | 1/2011 |
| JP | 07-053330 | 2/1995 |

(Continued)

OTHER PUBLICATIONS

U.S. Appl. No. 14/604,776, filed Jan. 26, 2015, Steven Daryl Smith et al.
U.S. Appl. No. 14/604,778, filed Jan. 26, 2015, Steven Daryl Smith et al.
U.S. Appl. No. 14/604,779, filed Jan. 26, 2015, Yonas Gizaw et al.
U.S. Appl. No. 14/604,781, filed Jan. 26, 2015, Carola Barrera et al.
International Search Report and Written Opinion dated Oct. 15, 2013, 9 pgs.
International Search Report and Written Opinion dated Oct. 30, 2013, 8 pgs.
International Search Report and Written Opinion dated Oct. 30, 2013, 9 pgs.
International Search Report and Written Opinion dated Oct. 18, 2013, 9 pgs.

*Primary Examiner* — Marc S Zimmer
(74) *Attorney, Agent, or Firm* — Jason J Camp

(57) ABSTRACT

Nonwoven fabrics comprising an organopolysiloxane polymer coating that can impart softness to said nonwoven fabric surface. Also disclosed are disposable absorbent articles comprising said nonwoven fabrics.

10 Claims, No Drawings

(56) References Cited

U.S. PATENT DOCUMENTS

| | | |
|---|---|---|
| 2004/0029981 A1 | 2/2004 | Herzig et al. |
| 2004/0048996 A1 | 3/2004 | Lange |
| 2004/0092424 A1 | 5/2004 | Boutique et al. |
| 2004/0092425 A1 | 5/2004 | Boutique et al. |
| 2004/0138400 A1 | 7/2004 | Lange |
| 2005/0009721 A1 | 1/2005 | Delplancke et al. |
| 2005/0170994 A1 | 8/2005 | Casado-Domingues et al. |
| 2006/0235181 A1 | 10/2006 | Lange et al. |
| 2007/0020452 A1 * | 1/2007 | Hamed ............... D06M 13/005 428/359 |
| 2007/0041929 A1 | 2/2007 | Torgerson |
| 2007/0041930 A1 | 2/2007 | Meder et al. |
| 2009/0142293 A1 | 6/2009 | Wagner et al. |
| 2010/0041583 A1 | 2/2010 | Ponder et al. |
| 2010/0215604 A1 | 8/2010 | Van Flordrop et al. |
| 2010/0247472 A1 | 9/2010 | Sau |
| 2011/0135588 A1 | 6/2011 | Uehara |
| 2012/0037040 A1 | 2/2012 | Standke et al. |
| 2012/0276175 A1 | 11/2012 | Dihora |
| 2014/0020188 A1 | 1/2014 | Gizaw et al. |
| 2014/0024780 A1 | 1/2014 | Benlahmar et al. |
| 2014/0030206 A1 | 1/2014 | Smith et al. |
| 2014/0128521 A1 | 5/2014 | Sekiya et al. |
| 2014/0206805 A1 | 7/2014 | Sekiya et al. |
| 2015/0225313 A1 | 8/2015 | Schmidt et al. |
| 2015/0307417 A1 | 10/2015 | Schmidt et al. |

FOREIGN PATENT DOCUMENTS

| | | |
|---|---|---|
| JP | 07-053331 | 2/1995 |
| JP | 07-053332 | 2/1995 |
| JP | 2002-308723 A | 10/2002 |
| JP | A-2002-308991 | 10/2002 |
| JP | 05-320349 | 10/2013 |
| WO | WO9818870 A1 | 3/1998 |
| WO | WO9932539 A1 | 7/1999 |
| WO | WO 2000/71806 | 11/2000 |
| WO | WO 2002/018528 | 3/2002 |
| WO | WO 2004/041987 | 5/2004 |
| WO | WO 2005/009721 A1 | 2/2005 |
| WO | WO 2011/123727 A | 10/2011 |
| WO | WO 2014/018985 | 1/2014 |

\* cited by examiner

† cited by third party

ABSORBENT ARTICLES COMPRISING ORGANOPOLYSILOXANE CONDITIONING POLYMERS

FIELD OF THE INVENTION

The present invention relates to disposable absorbent articles comprising an inventive organopolysiloxane surface coating disposed onto at least one component. The surface coating imparts a softer feel to such articles or treated components thereof.

BACKGROUND OF THE INVENTION

Sanitary tissue products and nonwoven fabrics find uses in many product areas including disposable cleaning products and disposable absorbent articles. Sanitary tissue products and nonwoven fabrics are useful in the area of lotioned wipes that generally include a nonwoven that has been pretreated with an aqueous or non-aqueous composition such as baby-wipes, hard-surface cleaning wipes and the like. Nonwovens are also useful in the area of un-lotioned wipes that generally include the nonwoven as the finished product such as paper-towels and other disposable wiping product. Unlotioned wipes products may optionally include a surface treatment to modify the abrasive or scrubbing properties of the nonwoven that may increase the abrasiveness for harder cleaning jobs or reduce the abrasiveness for gentler cleaning jobs. Nonwovens are also useful in the area of absorbent articles, which are generally assembled from a combination of nonwovens and/or film materials. Sanitary tissue products are used are wiping instruments in bathrooms, kitchens, or other uses for cleaning surfaces.

In any of the product areas in which nonwovens and sanitary tissue products are generally useful, it can be desirable to increase the softness of the nonwoven or sanitary tissue product itself. For example, individuals, parents and caregivers naturally seek to provide as much comfort as they can for themselves and for their babies, and utilizing products such as lotioned cleaning wipes, un-lotioned cleaning wipes, disposable diapers and the like that they perceive as relatively soft provides reassurance that they are doing what they can to provide comfort in that context. The same can be said of other types of cleaning wipes and/or disposable absorbent articles that are designed to be used on, applied to and/or worn close the skin or used on delicate surfaces, such as facial wipes, hard-surface wipes, fabric-cleaning wipes, training pants, adult incontinence undergarments, feminine hygiene products, breast pads, care mats, bibs, and wound dressing products, a soft hand feel can reassure the wearer or caregiver that the article will be gentle to the treated surface and/or comfortable against the skin.

Many manufacturers thus devote efforts toward enhancing the softness of the various materials used to make such products, such as various web materials, including nonwoven web materials formed from polymer fibers, and laminates thereof, forming the products. Various efforts have been made to provide or alter features of nonwoven web materials and sanitary tissue products with the objective of enhancing consumer perceptions of softness. These efforts have included selection and/or manipulation of fiber chemistry, basis weight, loft, fiber density, configuration and size, tinting and/or opacifying, embossing or bonding in various patterns, and the like.

These approaches have had varying degrees of success, but have left room for improvement in enhancing the softness of such disposable absorbent articles. Accordingly, it would be desirable to provide an alternative to those disposable absorbent articles already known in the art.

SUMMARY OF THE INVENTION

The present invention relates to nonwovens and sanitary tissue products having a soft feel and consumer products comprising said nonwovens or sanitary tissue paper. The nonwovens or sanitary tissue paper comprise an inventive organopolysiloxane polymer surface coating that is disposed onto at least one portion of the nonwoven or sanitary tissue paper. The surface coating imparts a softer feel to such nonwovens or treated portions thereof.

The present invention attempts to solve one or more of the aforementioned needs by providing, in one aspect, nonwovens and sanitary tissue products comprising an inventive organopolysiloxane conditioning polymer. The invention also relates to methods of making such articles and to methods of using them.

The inventive organopolysiloxane polymer is functionalized to favorably deposit onto one or more article surfaces to provide a softness benefit. The inventive polymer's charge density can be custom-tailored to enhance durability, deposition and conditioning (e.g., soft feel) performance in different use environments. Further, by varying the inventive polymer's functionalization, including by controlling charge density and/or hydrophobic substitution and/or hydrophilic substitution, the inventive polymer can be custom-tailored for a variety of product formulations and uses.

In one aspect of the invention, the consumer product is a surface treatment wipe such as a cleaning wipe.

In one aspect of the invention, the consumer product is a work article. The work article may be an absorbent article or may not be an absorbent article such as a gown or shoe or other garment.

In one aspect of the invention, the consumer product is a disposable absorbent article is a baby diaper having a containment assembly that comprises a topsheet, a backsheet, and an absorbent core disposed between the topsheet and the backsheet. The backsheet comprises a nonwoven web positioned at the outermost portion of the absorbent article, for covering at least a portion of the outermost portion of the absorbent core of the article.

The present invention also relates to disposable absorbent articles such as training pants, adult incontinence articles, feminine protection articles (e.g., sanitary napkins, catamenial tampons), disposable surgical or medical garments (e.g., gowns, drapes, shoe covers, and caps), bed pads, incontinent pads, towels, wipes (e.g., for car cleaning, lens cleaning, packaging, cleaning, and dust), packing materials, disposable garments (e.g., underwear), absorbent bandages, wound dressings, and the like.

The present invention also relates to disposable absorbent articles such as bathroom tissue, kitchen towels, paper towels, napkins, wipes including baby wipes, facial wipes, and other hard surface cleaning wipes.

DETAILED DESCRIPTION OF THE INVENTION

The present invention provides a nonwoven fabric and sanitary tissue products comprising a blocky cationic organopolysiloxane having the formula:

$$M_w D_x T_y Q_z$$

wherein:

M=[SiR$_1$R$_2$R$_3$O$_{1/2}$], [SiR$_1$R$_2$G$_1$O$_{1/2}$], [SiR$_1$G$_1$G$_2$O$_{1/2}$], [SiG$_1$G$_2$G$_3$O$_{1/2}$], or combinations thereof;

D=[SiR$_1$R$_2$O$_{2/2}$], [SiR$_1$G$_1$O$_{2/2}$], [SiG$_1$G$_2$O$_{2/2}$] or combinations thereof;

T=[SiR$_1$O$_{3/2}$], [SiG$_1$O$_{3/2}$] or combinations thereof;

Q=[SiO$_{4/2}$];

w=is an integer from 1 to (2+y+2z);
x=is an integer from 5 to 15,000;
y=is an integer from 0 to 98;
z=is an integer from 0 to 98;

R$_1$, R$_2$ and R$_3$ are each independently selected from the group consisting of H, OH, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, C$_1$-C$_{32}$ alkoxy, C$_1$-C$_{32}$ substituted alkoxy, C$_1$-C$_{32}$ alkylamino, and C$_1$-C$_{32}$ substituted alkylamino;

at least one of M, D, or T incorporates at least one moiety G$_1$, G$_2$ or G$_3$; and G$_1$, G$_2$, and G$_3$ are each independently selected from the formula:

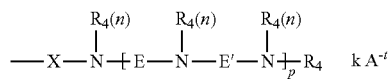

wherein:

X comprises a divalent radical selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide, and ring-opened glycidyl, with the proviso that if X does not comprise a repeating alkylene oxide moiety then X can further comprise a heteroatom selected from the group consisting of P, N and O. Alternatively, each X can be a divalent radical independently selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, and C$_6$-C$_{32}$ substituted arylalkylene;

N=a nitrogen atom;

R$_4$ comprises identical or different monovalent radicals selected from the group consisting of H, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, and C$_6$-C$_{32}$ substituted alkylaryl;

E comprises a divalent radical selected from the group consisting of C$_1$-C$_{32}$ alkylene or C$_3$-C$_{32}$ alkylene, C$_1$-C$_{32}$ substituted alkylene or C$_3$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy or C$_3$-C$_{32}$ alkoxy, C$_1$-C$_{32}$ substituted alkoxy or C$_3$-C$_{32}$ substituted alkoxy, C$_1$-C$_{32}$ alkyleneamino or C$_3$-C$_{32}$ alkyleneamino, C$_1$-C$_{32}$ substituted alkyleneamino or C$_3$-C$_{32}$ substituted alkyleneamino, ring-opened epoxide and ring-opened glycidyl, with the proviso that if E does not comprise a repeating alkylene oxide moiety then E can further comprise a heteroatom selected from the group consisting of P, N, and O;

E' comprises a divalent radical selected from the group consisting of C$_1$-C$_{32}$ alkylene or C$_3$-C$_{32}$ alkylene, C$_1$-C$_{32}$ substituted alkylene or C$_3$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy or C$_3$-C$_{32}$ alkoxy, C$_1$-C$_{32}$ substituted alkoxy or C$_3$-C$_{32}$ substituted alkoxy, C$_1$-C$_{32}$ alkyleneamino or C$_3$-C$_{32}$ alkyleneamino, C$_1$-C$_{32}$ substituted alkyleneamino or C$_3$-C$_{32}$ substituted alkyleneamino, ring-opened epoxide and ring-opened glycidyl, with the proviso that if E' does not comprise a repeating alkylene oxide moiety then E' can further comprise a heteroatom selected from the group consisting of P, N, and O;

In one embodiment, there are no E moieties that are ethylene moieties. Each E and E' can be an identical or different radicals. In some embodiments, E and E' are different radicals.

In some embodiments, at least one E or E' is independently selected from the group consisting of:

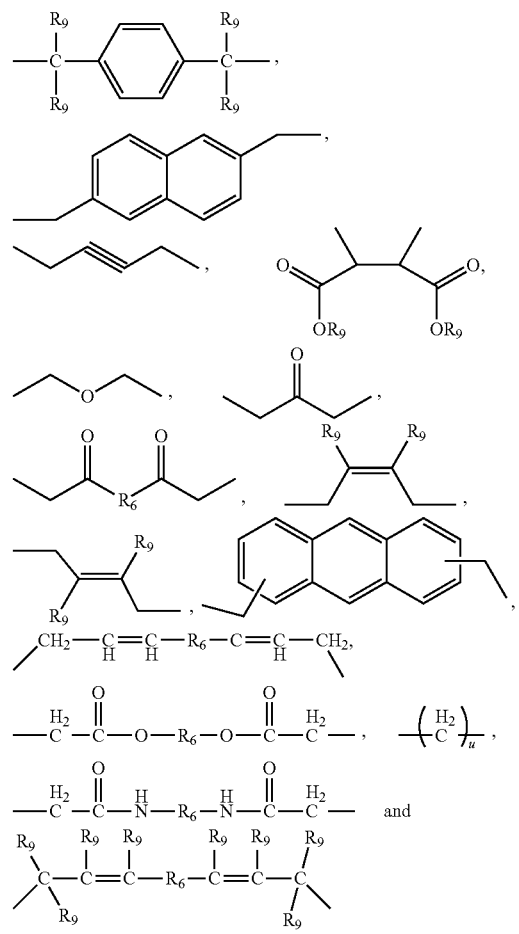

wherein:

R$_6$ comprises a divalent radical selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide, and ring-opened glycidyl, with the proviso that if R$_6$ does not comprise a repeating alkylene oxide moiety then R$_6$ can further comprise a heteroatom selected from the group consisting of P, N, and O;

R$_9$ comprises identical or different monovalent radicals selected from the group consisting of H, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or $C_6$-$C_{32}$ substituted aryl, $C_6$-$C_{32}$ alkylaryl, and $C_6$-$C_{32}$ substituted alkylaryl; and u is an integer independently selected from 3 to 32.

One or more E or E' radical can be an ethylene radical, so long as at least one E or E'radical in the organopolysiloxane polymer is a radical with 3 or more carbon atoms.

Each $R_4$ can be different radicals, and in some embodiments at least one $R_4$ is a methyl radical. In one embodiment $R_4$ is a methyl group or a hydrogen.

p is an integer independently selected from 2 to 100;

n is an integer independently selected from 1 or 2;

when at least one of $G_1$, $G_2$, or $G_3$ is positively charged, $A^{-t}$ is a suitable charge balancing anion or anions such that the total charge, k, of the charge-balancing anion or anions is equal to and opposite from the net charge on the moiety $G_1$, $G_2$ or $G_3$;

where t is an integer independently selected from 1, 2, or 3; and k≤p*2/t+1 such that the total number of cationic charges balances the total number of anionic charges in the organopolysiloxane molecule. $A^{-t}$ can be selected from the group consisting of $Cl^-$, $Br^-$, $I^-$, methylsulfate, toluene sulfonate, carboxylate, phosphate, hydroxide, acetate, formate, carbonate, nitrate, and combinations thereof; or alternatively from the group consisting of $Cl^-$, $Br^-$, $I^-$, methylsulfate, toluene sulfonate, carboxylate, phosphate and combinations thereof.

The organopolysiloxane can have a charge density of from 0.04 meq/g to 12 meq/g, or from 0.04 meq/g to 4 meq/g; or from 1 meq/g to 12 meq/g. In some embodiments, w is an integer from 2 to 50, and in others w is equal to 2. In particular embodiments, x is an integer from 10 to 4,000, or from 40 to 2,000. In one embodiment, w is equal to 2, x is an integer from 20 to 1,000, and y and z are 0.

In one embodiment, $G_1$, $G_2$ and $G_3$ are identical; in another embodiment, $G_1$ and $G_2$ are the same while $G_3$ is different; and in another embodiment, each of $G_1$, $G_2$, and $G_3$ are different. For at least one of $G_1$, $G_2$ or $G_3$, m can be an integer independently selected from 2 to 50, or from 2 to 25, or from 2 to 10. Or, for at least one of $G_1$, $G_2$ or $G_3$, k can be an integer independently selected from 0 to 101, or from 2 to 50. In at least one embodiment, y=z=0. In some embodiments, from 50% to 100% of the amines present in the molecule can be quaternized, or from 70% to 100%, or from 90% to 100%.

One skilled in the art will recognize that the blocky organopolysiloxane of the present invention encompasses a plethora of different embodiments. To this end, when both y and z equal zero, the blocky organopolysiloxane of the present invention can be represented by the formula:

$M_w D_x$ where:
M=[$SiR_1R_2R_3O_{1/2}$], [$SiR_1R_2G_1O_{1/2}$], [$SiR_1G_1G_2O_{1/2}$], [$SiG_1G_2G_3O_{1/2}$], or combinations thereof;
D=[$SiR_1R_2O_{2/2}$];
w=is an integer from 1 to 2;
x=is an integer from 5 to 15,000;
$R_1$, $R_2$ and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy, $C_1$-$C_{32}$ alkylamino, and $C_1$-$C_{32}$ substituted alkylamino;
at least one of M or D incorporates at least one moiety $G_1$, $G_2$ or $G_3$, and $G_1$, $G_2$, and $G_3$ are each independently selected from:

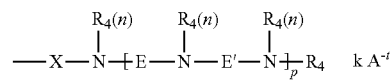

wherein:

X comprises a divalent radical selected from the group consisting of $C_1$-$C_{32}$ alkylene, $C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide and ring-opened glycidyl, with the proviso that if X does not comprise a repeating alkylene oxide moiety then X can further comprise a heteroatom selected from the group consisting of P, N, and O. Alternatively, each X can be a divalent radical independently selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, and $C_6$-$C_{32}$ substituted arylalkylene;

$R_4$ comprises identical or different monovalent radicals selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl;

E comprises a divalent radical selected from the group consisting of $C_1$-$C_{32}$ alkylene or $C_3$-$C_{32}$ alkylene, $C_1$-$C_{32}$ substituted alkylene or $C_3$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy or $C_3$-$C_{32}$ alkoxy, $C_1$-$C_{32}$ substituted alkoxy or $C_3$-$C_{32}$ substituted alkoxy, $C_1$-$C_{32}$ alkyleneamino or $C_3$-$C_{32}$ alkyleneamino, $C_1$-$C_{32}$ substituted alkyleneamino or $C_3$-$C_{32}$ substituted alkyleneamino, ring-opened epoxide and ring-opened glycidyl, with the proviso that if E does not comprise a repeating alkylene oxide moiety then E can further comprise a heteroatom selected from the group consisting of P, N, and O;

E' comprises a divalent radical selected from the group consisting of $C_1$-$C_{32}$ alkylene or $C_3$-$C_{32}$ alkylene, $C_1$-$C_{32}$ substituted alkylene or $C_3$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy or $C_3$-$C_{32}$ alkoxy, $C_1$-$C_{32}$ substituted alkoxy or $C_3$-$C_{32}$ substituted alkoxy, $C_1$-$C_{32}$ alkyleneamino or $C_3$-$C_{32}$ alkyleneamino, $C_1$-$C_{32}$ substituted alkyleneamino or $C_3$-$C_{32}$ substituted alkyleneamino, ring-opened epoxide and ring-opened glycidyl, with the proviso that if E' does not comprise a repeating alkylene oxide moiety then E' can further comprise a heteroatom selected from the group consisting of P, N, and O;

In one embodiment, there are no E moieties that are ethylene moieties. Each E and E' can be an identical or different radicals. In some embodiments, E and E' are different radicals.

In some embodiments, at least one E or E' is independently selected from the group consisting of:

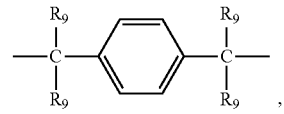

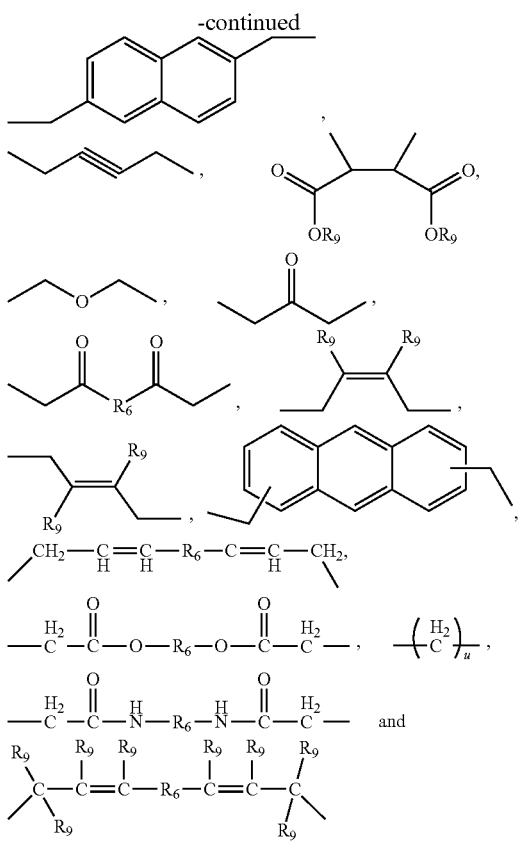

wherein:

$R_6$ comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if $R_6$ does not comprise a repeating alkylene oxide moiety then $R_6$ can further comprise a heteroatom selected from the group consisting of P, N, and O;

$R_9$ comprises identical or different monovalent radicals selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl; and u is an integer independently selected from 3 to 32.

One or more E or E' radical can be an ethylene radical, so long as at least one E or E' radical in the organopolysiloxane polymer is a radical with 3 or more carbon atoms.

Each $R_4$ can be different radicals, and in some embodiments at least one $R_4$ is a methyl radical. In one embodiment $R_4$ is a methyl group or a hydrogen.

p is an integer independently selected from 2 to 100;
n is an integer independently selected from 1 or 2;
when at least one of $G_1$, $G_2$, or $G_3$ is positively charged, $A^{-t}$ is a suitable charge balancing anion or anions such that the total charge, k, of the charge-balancing anion or anions is equal to and opposite from the net charge on the moiety $G_1$, $G_2$ or $G_3$;

where t is an integer independently selected from 1, 2, or 3; and $k \leq (p*2/t)+1$ such that the total number of cationic charges balances the total number of anionic charges in the organopolysiloxane molecule. $A^{-t}$ can be selected from the group consisting of Cl⁻, Br⁻, I⁻, methylsulfate, toluene sulfonate, carboxylate, phosphate, hydroxide, acetate, formate, carbonate, nitrate, and combinations thereof; or alternatively from the group consisting of Cl⁻, Br⁻, I⁻, methylsulfate, toluene sulfonate, carboxylate, phosphate and combinations thereof.

In one embodiment, E or E' is a primary alkyl chain having 3 or more carbon atoms, or 4 or more carbon atoms, or 5 or more carbon atoms, or from 4 to 32 carbon atoms. Without being limited by theory, it is believed that in embodiments where E or E' is a primary alkyl chain having exactly 2 carbon atoms, the moiety G can be unstable relative to the potential for an elimination reaction. This is because an undesirable elimination reaction is likely to take place, due to an unshared electron pair reacting to create an alkene.

In another embodiment, the moiety E or E' can be independently selected from different groups of different length to control the spacing and density of the charges along the chain. In certain applications, it can be desirable to have these charges closely spaced, and in other applications it can be desirable to have these charges spaced farther apart. The charged moiety G can be separate from the silicone portion of the organopolysiloxane, and more specifically, disposed at the terminal ends of the siloxane moiety. Without being bound by theory, it is believed that maintaining the charges in a "blocky" fashion disposed at the ends of a terminal siloxane moiety, allows the siloxane moiety to project further out from the surface of the treated substrate, resulting in a more lubricious, softer feel for the treated substrate.

In one embodiment, the invention provides an dry absorbent article comprising the inventive nonwoven fabric or sanitary paper product of the present invention. The absorbent article is selected from the group consisting of towels, towelettes, surface-cleaning wipes, fabric cleaning wipes, skin cleansing wipes, make-up removal wipes, applicator wipes, car cleaning wipes, lens cleaning wipes, packaging materials, cleaning wipes, dusting wipes, packing materials, disposable garments, disposable surgical or medical garments, bandages, and wound dressings.

In another embodiment, the invention provides an premoistened article comprising an inventive nonwoven fabric or sanitary paper product selected from the group consisting of towels, towelettes, surface-cleaning wipes, fabric cleaning wipes, skin cleansing wipes, make-up removal wipes, applicator wipes, car cleaning wipes, lens cleaning wipes, packaging materials, cleaning wipes, dusting wipes, packing materials, disposable garments, disposable surgical or medical garments, bandages, and wound dressings.

The absorbent article can be a disposable absorbent article selected from the group consisting of baby diapers, training pants, adult incontinence articles, feminine protection articles, bed pads, incontinent pads, absorbent bandages, and wound dressings. In one embodiment, the disposable absorbent article comprises a topsheet, wherein said topsheet comprises the inventive nonwoven fabric. The disposable absorbent article can also comprise a backsheet comprising the inventive nonwoven fabric. Further, the disposable absorbent article can comprise a barrier cuff, wherein said barrier cuff comprises the inventive nonwoven fabric.

In some embodiments, the nonwoven fabric comprises less than 1 gram per square meter (gsm), or from 0.01-20 gsm, or from 0.01-10 gsm, or from 0.01-5 gsm, of organopolysiloxane after said nonwoven fabric is dried.

In a method of making the nonwoven fabric or sanitary paper product, the organopolysiloxane can be blended with a carrier prior to being applied to the nonwoven. The carrier can comprise in one aspect water, ethanol, and/or isopropanol. Alternatively, the carrier can be organic. In a particular embodiment, the carrier is a volatile carrier. In some embodiments, the carrier comprises water and the organopolysiloxane is emulsified with the water prior to application to the nonwoven fabric or sanitary paper product.

In another aspect, the invention provides a method of treating a surface, comprising contacting said surface with the one or more embodiments of the inventive nonwoven fabric or sanitary paper product or an absorbent article comprising such non-woven fabric or sanitary paper product.

Features and benefits of the various embodiments of the present invention will become apparent from the following description, which includes examples of specific embodiments intended to give a broad representation of the invention. Various modifications will be apparent to those skilled in the art from this description and from practice of the invention. The scope is not intended to be limited to the particular forms disclosed and the invention covers all modifications, equivalents, and alternatives falling within the spirit and scope of the invention as defined by the claims.

I. Definitions

As used herein, the term "soft" refers to the aesthetically desirable tactile sensation of softness.

"Fiber" as used herein means an elongate particulate having an apparent length greatly exceeding its apparent diameter, i.e. a length to diameter ratio of at least 10. Fibers having a non-circular cross-section are common; the "diameter" in this case may be considered to be the diameter of a circle having cross-sectional area equal to the cross-sectional area of the fiber. More specifically, as used herein, "fiber" refers to fibrous structure-making fibers. The present invention contemplates the use of a variety of fibrous structure-making fibers, such as, for example, natural fibers, including wood fibers, or synthetic fibers made from natural polymers and/or synthetic fibers, or any other suitable fibers, and any combination thereof.

"Fibrous structure" as used herein means a structure (web) that comprises one or more fibers. Nonlimiting examples of processes for making fibrous structures include known wet-laid fibrous structure making processes, air-laid fibrous structure making processes, meltblowing fibrous structure making processes, co-forming fibrous structure making processes, and spunbond fibrous structure making processes. Such processes typically include steps of preparing a fiber composition, oftentimes referred to as a fiber slurry in wet-laid processes, either wet or dry, and then depositing a plurality of fibers onto a forming wire or belt such that an embryonic fibrous structure is formed, drying and/or bonding the fibers together such that a fibrous structure is formed, and/or further processing the fibrous structure such that a finished fibrous structure is formed. The fibrous structure may be a through-air-dried fibrous structure and/or conventionally dried fibrous structure. The fibrous structure may be creped or uncreped. The fibrous structure may exhibit differential density regions or may be substantially uniform in density. The fibrous structure may be pattern densified, conventionally felt-presses and/or high-bulk, uncompacted. The fibrous structures may be homogenous or multilayered in construction.

After and/or concurrently with the forming of the fibrous structure, the fibrous structure may be subjected to physical transformation operations such as embossing, calendering, selfing, printing, folding, softening, ring-rolling, applying additives, such as latex, lotion and softening agents, combining with one or more other plies of fibrous structures, and the like to produce a finished fibrous structure that forms and/or is incorporated into a sanitary tissue product.

"Sanitary tissue product" as used herein means a wiping implement for post-urinary and/or post-bowel movement cleaning (toilet tissue), for otorhinolaryngological discharges (facial tissue) and/or multi-functional absorbent and cleaning uses (absorbent towels such as paper towels and/or wipes). The sanitary tissue products of the present invention may comprise one or more fibrous structures and/or finished fibrous structures. The sanitary tissue products of the present invention may be in any suitable form, such as in a roll, in individual sheets, in connected, but perforated sheets, in a folded format or even in an unfolded.

"Wipe" refers to any substrate-based product used in contact with a surface to be treated. A wipe may be lotioned or un-lotioned. A wipes may be used to clean a surface or to otherwise treat the surface. The surface may be a physiological surface such as the skin or may be a non-physiological surface such as a household surface.

The terms "fiber" and "filament" are used interchangeably.

The terms "nonwoven", "nonwoven fabric", fibrous structure" and "nonwoven web" are used interchangeable.

The term "plurality of fibers" refers to fibers or filaments as well as to nonwoven fabrics.

The term "charge density", as used herein, refers to the ratio of the number of positive charges on a monomeric unit of which a polymer is comprised to the molecular weight of said monomeric unit. The charge density multiplied by the polymer molecular weight determines the number of positively charged sites on a given polymer chain. This can also be expressed as:

$$\text{charge density} = \frac{(\text{moles of N}) \times (\text{charge per N})}{(\text{moles of polymer}) \times (\text{molecular wt. of polymer})} \times 100$$

As used herein, the term "absorbent article" refers to devices which absorb and contain body exudates, and more specifically, refers to devices which are placed against or in proximity to the body of the wearer to absorb and contain the various exudates discharged from the body. Such devices include, but are not limited to, diapers, training pants, adult incontinence products, sanitary napkins, and pantiliners.

As used herein, the term "diaper" refers to an absorbent article generally worn by infants, and incontinent persons that is worn about the lower torso of the wearer. In other words, the term "diaper" includes infant diapers, training pants, adult incontinence devices, etc.

As used herein, the term "disposable" refers to absorbent articles which generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "volatile" means a material having a vapor pressure (VP) of from 0.0001 torr to 100 torr, as measured at 25° C.

As used herein "consumer product" means baby care, personal care, fabric & home care, family care (e.g., facial tissues, paper towels), feminine care, health care, beauty care and like products generally intended to be used or consumed in the form in which they are sold. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, and tooth whitening.

As used herein, the term "cleansing and/or treatment composition" is a subset of consumer products that includes, unless otherwise indicated, personal care, fabric care, and home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening. The care agents can advantageously be used in household polishes and cleaners for floors and countertops to provide benefits such as enhanced shine. Care agents in fabric softeners can help preserve "newness" because of their softening properties, and those having elasticity can help smooth out wrinkles. The care agents can also enhance shoe cleaning and polishing products.

As used herein, the term "personal care cleansing and/or treatment composition" is a subset of cleaning and treatment compositions that includes, unless otherwise indicated, products for treating hair, including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products; liquid cleaning and disinfecting agents including antibacterial hand-wash types, cleaning bars, mouthwashes, denture cleaners, and dentifrice cleaners; hair shampoos and hair-rinses; shower gels, fine fragrances, and foam baths; substrate-laden products such as dry and wetted wipes and pads, nonwoven substrates, and sponges; as well as sprays and mists all for consumer or/and institutional use; and/or methods relating to oral care including toothpastes, tooth gels, tooth rinses, denture adhesives, and tooth whitening.

As used herein, the term "fabric and/or hard surface cleansing and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products, as applicable, may be in standard, concentrated or even highly concentrated form even to the extent that such products may in certain aspects be non-aqueous.

As used herein, articles such as "a" and "an" are understood to mean one or more of what is claimed or described.

As used herein, the terms "include", "contain", and "have" are non-limiting and do not exclude other components or features beyond those expressly identified in the description or claims.

As used herein, the terms "treatment agent", "benefit agent", "active", "active agent", and/or "care agent" and the like are used interchangeably to mean materials that can impart desirable aesthetic and/or functional properties (e.g., conditioning benefits such as softening or freshening) to a substrate. For example, the inventive organopolysiloxane polymer of the present invention can be used as a conditioning agent to impart conditioning benefits to substrates.

As used herein, the terms "conditioning agent" and "conditioning aid" are used interchangeably to refer to a material that delivers desirable conditioning effects (e.g., benefits such as softening or freshening) to a substrate. Conditioning agents are a type of treatment agent.

As used herein, the term "conditioning polymer" means a polymer that delivers desirable conditioning effects (e.g., softening or freshening) to a substrate.

As used herein, the term "situs" and "surface" are used interchangeably. Non-limiting examples of surfaces include surfaces that are being treated by the products of the present invention.

As used herein, "adjunct" means an optional material that can be added to a composition to complement the aesthetic and/or functional properties of the composition.

As used herein, "auxiliary composition" refers to one or more compositions that when combined with a benefit agent emulsion of the present invention, form a consumer product composition. The auxiliary composition may be in the form of one or more ingredients or ingredient combinations.

As used herein, "carrier" means an optional material, including but not limited to a solid or fluid, that can be combined with a benefit agent (e.g., conditioning polymers) to facilitate delivery and/or use of the benefit agent.

As used herein, the term "solid" includes granular, powder, bar and tablet product forms.

As used herein, the term "fluid" includes liquid, gel, paste and gas product forms including unitized-dose forms that generally include a fluid composition enclosed in a pouch or other delivery vehicle.

As used herein, the term "particle" includes solid and semi-solid particles, as well as emulsion droplets.

Unless otherwise indicated, all percentages and ratios herein are by weight.

All percentages and ratios are calculated based on the weight of the total composition unless otherwise indicated.

Unless specified otherwise, all molecular weights are given in Daltons.

Unless otherwise indicated, all molecular weights are weight average molecular weights as determined by size exclusion chromatography using a MALS detector (SEC-MALS), as is commonly known by those skilled in the art. A MALS detector (Multi-Angle Light Scattering Detector, such as those manufactured by Malvern Instruments Ltd., Malvern, UK) determines absolute molecular weight, rather than relative molecular weight (i.e., determined relative to a standard).

Unless otherwise noted, all component (i.e., ingredient) or composition levels are in reference to the active portion of that component or composition, and are exclusive of impurities, for example, residual solvents or by-products, which may be present in commercially available sources of such components or compositions.

As used herein, the term "hydrocarbon polymer radical" means a polymeric radical comprising only carbon and hydrogen.

As used herein, "ethylene moiety" means a divalent $CH_2CH_2$ moiety.

As used herein, the term "siloxyl residue" means a polydialkylsiloxane moiety.

As used herein, the nomenclature $SiO_n/2$ represents the ratio of oxygen and silicon atoms. For example, $SiO1/2$ means that, on average, one oxygen atom is shared between two silicon atoms. Likewise $SiO2/2$ means that, on average, two oxygen atoms are shared between two silicon atoms and $SiO3/2$ means that, on average, three oxygen atoms are shared between two silicon atoms.

As used herein, the terms "substantially no", "substantially free of", and/or "substantially free from" mean that the indicated material is at the very minimum not deliberately added to the composition to form part of it, or, preferably, is not present at analytically detectable levels. It is meant to include compositions whereby the indicated material is present only as an impurity in one of the other materials deliberately included.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

II. Nonwoven Fabrics

A nonwoven fabric is a manufactured sheet, web or batt of directionally or randomly orientated fibers, bonded by friction, and/or cohesion and/or adhesion, including paper products which are generally formed from cohesion and/or adhesion of cellulose fibers. The fibers may be of natural or man-made origin. They may be staple or continuous filaments or be formed in situ.

Nonwovens can be formed by many processes such as meltblowing, spunbonding, carded, air-laying, wet-laying, co-forming and the like. The basis weight of nonwoven fabrics is usually expressed in grams per square meter (gsm). Commercially available fibers have diameters ranging from less than 0.001 mm to more than 0.2 mm and they come in several different forms: short fibers (known as staple, or chopped), continuous single fibers (filaments or monofilaments), untwisted bundles of continuous filaments (tow), and twisted bundles of continuous filaments (yam). Fibers are classified according to their origin, chemical structure, or both. They can be braided into ropes and cordage, made into felts (also called nonwovens or nonwoven fabrics), woven or knitted into textile fabrics, or, in the case of high-strength fibers, used as reinforcements in composites—that is, products made of two or more different materials.

The nonwovens may comprise fibers made by nature (natural fibers), made by man (synthetic or man-made), or combinations thereof. Example natural fibers include but are not limited to: cellulose fibers, wood fibers, animal fibers such as wool, silk, fur, and hair; vegetable fibers such as cellulose, cotton, flax, linen, and hemp; and certain naturally occurring mineral fibers. Synthetic fibers can be derived from natural fibers. Example synthetic fibers, which are derived from natural fibers include but are not limited to rayon and lyocell, both of which are derived from cellulose, a natural polysaccharide fiber. Synthetic fibers, which are not derived from natural fibers can be derived from other natural sources or from mineral sources. Example synthetic fibers not derived from natural sources include but are not limited to polysaccharides such as starch. Example fibers from mineral sources include but are not limited to polyolefin fibers such as polypropylene, polyethylene fibers and polyester, which are derived from petroleum, and silicate fibers such as glass and asbestos.

The fibrous structures of the present invention may comprise, in addition to fibers, an optional additive selected from the group consisting of permanent and/or temporary wet strength resins, dry strength resins, wetting agents, lint resisting agents, absorbency-enhancing agents, immobilizing agents, especially in combination with emollient lotion compositions, antiviral agents including organic acids, antibacterial agents, polyol polyesters, antimigration agents, polyhydroxy plasticizers, softening agents, lotions and mixtures thereof.

Such optional additives may be added to the fiber furnish, the embryonic fibrous web and/or the fibrous structure. Such optional additives may be present in the fibrous structures at any level based on the dry weight of the fibrous structure. The optional additives may be present in the fibrous structures at a level of from 0.001 to 50% and/or from 0.001 to 20% and/or from 0.01 to 5% and/or from 0.03 to 3% and/or from 0.1 to 1.0% by weight, on a dry fibrous structure basis.

Processes for Making Nonwoven Structures

The fibrous structures of the present invention may be made by any suitable process known in the art.

Nonwoven webs can be formed by direct extrusion processes during which the fibers and webs are formed at about the same point in time, or by preformed fibers which can be laid into webs at a distinctly subsequent point in time. Example direct extrusion processes include but are not limited to: spunbonding, meltblowing, solvent spinning, electrospinning, and combinations thereof typically forming layers.

As used herein, the term "spunbonded fibers" refers to small diameter fibers, which are formed by extruding molten thermoplastic material as filaments from a plurality of fine, usually circular capillaries of a spinneret. Spunbond fibers are quenched and generally not tacky when they are deposited onto a collecting surface. Spunbond fibers are generally continuous.

As used herein, the term "meltblown fibers" means fibers formed by extruding a molten thermoplastic material through a plurality of fine, usually circular, die capillaries as molten threads or filaments into converging high velocity gas (e.g. air) streams, which attenuate the filaments of molten thermoplastic material to reduce their diameter. Thereafter, the meltblown fibers are carried by the high velocity gas stream and are deposited on a collecting surface to form a web of randomly disbursed meltblown fibers.

Example "laying" processes include wetlaying and drylaying. Example drylaying processes include but are not limited to airlaying, carding, and combinations thereof typically forming layers. Combinations of the above processes yield nonwovens commonly called hybrids or composites. Example combinations include but are not limited to spunbond-meltblown-spunbond (SMS), spunbond-carded (SC), spunbond-airlaid (SA), meltblown-airlaid (MA), and combinations thereof, typically in layers. Combinations which include direct extrusion can be combined at about the same point in time as the direct extrusion process (e.g., spinform and coform for SA and MA), or at a subsequent point in time. In the above examples, one or more individual layers can be created by each process. For instance, SMS can mean a three layer, 'sms' web, a five layer 'ssmms' web, or any reasonable variation thereof wherein the lower case letters designate individual layers and the upper case letters designate the compilation of similar, adjacent layers. The fibers in a nonwoven web are typically joined to one or more adjacent fibers at some of the overlapping junctions. This includes joining fibers within each layer and joining fibers between layers when there is more than one layer. Fibers can be joined by mechanical entanglement, by chemical bond or by combinations thereof.

In a preferred embodiment of the present invention, the nonwoven fabric is made of polypropylene (PP) and/or polyethylene (PET). In another embodiment the nonwoven fabric is made of bicomponent fibers consisting of PP and PET.

For use as core wrap material the nonwoven fabric is preferably made by a combination of spunbond and meltblown process (SMMS) and the basis weights are preferably from 7 gsm to 30 gsm, more preferably from 8 gsm to 20 gsm, and even more preferably from 8 gsm to 15 gsm. For use as topsheet material in the storage layer, the nonwoven fabric preferably comprises spunbond fibers. The basis weight of the topsheet is preferably from 10 to 30 gsm, more preferably from 15 to 20 gsm. In another embodiment, the topsheet comprises a carded nonwoven fabric with preferred basis weights from 10 gsm to 25 gsm, more preferably from 15 gsm to 20 gsm.

For application as acquisition material in the absorbent core, the nonwoven is preferably made by a carding process and the basis weights are preferably from 20 to 200 gsm, more preferably from 40 to 100 gsm and even more preferably 60 gsm. The material is further bonded, e.g. by resin-, or air-through thermal bonding processes.

III. Nonwoven Products

In one aspect, the present invention provides a nonwoven fabric comprising an inventive organopolysiloxane polymer coating that imparts a soft tactile feel to the coated surface. Nonwoven fabrics made of natural or synthetic fibers are commonly used in constructing consumer products including wipes and absorbent articles. In another aspect, the present invention provides a wipe and/or disposable absorbent article comprising a nonwoven fabric comprising the inventive organopolysiloxane polymer coating.

Although the detailed description that follows is primarily set forth in the context of a nonwoven fabric embodied in a disposable absorbent article, it should be understood that the present invention also has substantial utility in a wide variety of nonwoven products including products comprising lotioned and un-lotioned nonwovens such as towels, wipes (e.g., for car cleaning, lens cleaning, packaging, cleaning, and dust), packing materials, disposable garments (e.g., underwear), disposable surgical or medical garments (e.g., gowns, drapes, shoe covers, and caps), absorbent bandages, wound dressings, and the like, as well as a variety of absorptive devices, such as training pants, adult incontinence articles, feminine protection articles (e.g., sanitary napkins, catamenial tampons), bed pads, incontinent pads, and the like. Thus, the detailed description set forth below will allow one skilled in the art to readily adapt the invention to other articles, all of which are considered to be encompassed by the present invention.

Wipes

Wet wipes or wipes or wet-tissues are the general terms to describe a piece of material, generally non-woven material, used to cleanse body parts or hard surfaces. For example, most currently available wipes are intended for the cleaning of the perianal area after defecation. Such wipes include lotioned wipes such as baby-wipes and un-lotioned wipes such as sanitary tissue.

Other wipes are available for the cleansing, of the face or other body parts. Wipes are generally of sufficient dimension to allow for convenient handling while being small enough to be easily disposed of by the sewage system or discretely disposed of in garbage bins. The material of the wipes is generally flexible, potentially having a structured surface enhancing its cleaning performance. The material is generally a non-woven material, generally made of natural or synthetic compounds. The texture and material of the wipe can be of high relevance to the performance of the wipe.

In one embodiment of the present invention the nonwoven material comprises fibers made from a material selected from the group consisting of polyolefin, polyester, cellulose, rayon, polyamides, polyesteramide, polyvinyl alcohols, and combinations thereof. The substrate usable for this invention can be manufactured via any suitable process, such as but not limited to, spunlace process and preferably has a dry basis weight of between 45 grams per square meter (gsm) and 75 gsm, more preferably between 45 gsm and 65 gsm.

In another embodiment of the present invention the nonwoven material comprises wood fibers or a combination of wood fibers with a material selected from the group consisting of polyolefin, polyester, cellulose, rayon, polyamides, polyesteramide, polyvinyl alcohols, and combinations thereof.

Lotioned wipes are generally further impregnated with a liquid or semi liquid composition, intended to enhance the cleaning effectiveness of the wipe and/or to provide a smooth feeling. The liquid or semi-liquid composition may be aqueous or non-aqueous. Generally the composition is of sufficiently low viscosity to impregnate the entire structure of the wipe. In some other instances, the composition can be primarily present at the wipe surface and to a lesser extent in the inner structure of the wipe. In one optional embodiment the composition is releasably carried by the material, that is, the composition is contained either in or on a substrate and is readily releasable from the substrate by applying some force to the substrate, for example, wringing the substrate, or wiping a surface with the wet-wipe.

Absorbent Articles

Nonwoven fabrics made of natural or synthetic fibers are commonly used in constructing absorbent articles, for example, as topsheet material or as core wrap to enclose the storage layer of the absorbent core. In another aspect, the present invention provides a disposable absorbent article comprising a nonwoven fabric comprising the inventive organopolysiloxane polymer coating.

In one aspect, the disposable absorbent article is a baby diaper having a containment assembly that comprises a substantially liquid pervious topsheet, a substantially liquid impervious backsheet and an absorbent core located between the topsheet and the backsheet. The topsheet, backsheet, and/or other components of the diaper can be constructed from nonwoven fabric, which comprises an organopolysiloxane polymer surface coating which imparts softness to the nonwoven and thus to the diaper.

While the topsheet, the backsheet, and the absorbent core may be assembled in a variety of well-known configurations, preferred diaper configurations are described generally in U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet may be fully or partially elasticized or may be foreshortened to provide a void space between the topsheet and the absorbent core. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993. In some embodiments, the topsheet is an apertured topsheet such as those described in WO 95/05139 (Roe).

The backsheet may be joined with the topsheet. The backsheet prevents the exudates absorbed by the absorbent core and contained within the article from soiling other external articles that may contact the diaper, such as bed sheets and undergarments. In preferred embodiments, the backsheet is substantially impervious to liquids (e.g., urine) and comprises a laminate of a nonwoven and a thin plastic film such as a thermoplastic film having a thickness of 0.012 mm (0.5 mil) to 0.051 mm (2.0 mils) Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper while still preventing exudates from passing through the backsheet. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097.

The absorbent core generally is disposed between the topsheet and the backsheet. The absorbent core may comprise any absorbent material that is generally compressible, conformable, non-irritating to the wearer's skin, and capable of absorbing and retaining liquids such as urine and other certain body exudates. The absorbent core may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers, absorbent gelling materials, or any other known absorbent material or combinations of materials. The absorbent core may further comprise minor amounts (typically less than 10%) of non-liquid absorbent materials, such as adhesives, waxes, oils and the like.

The absorbent core preferably comprises an acquisition system, which comprises an upper acquisition layer facing towards the wearer and a lower acquisition layer. In one preferred embodiment the upper acquisition layer comprises a nonwoven fabric whereas the lower acquisition layer preferably comprises a mixture of chemically stiffened, twisted and curled fibers, high surface area fibers and thermoplastic binding fibers. In another preferred embodiment both acquisition layers are provided from a non-woven material, which is preferably hydrophilic.

Exemplary absorbent structures for use as the liquid storage structure are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989.

The acquisition layer preferably is in direct contact with the storage layer. The storage layer is preferably wrapped by a core wrap material. In one preferred embodiment the core wrap material comprises a top layer and a bottom layer. The top layer and the bottom layer can be provided from a non-woven material. One preferred material is a so-called "SMS" material, comprising a spunbonded, a melt-blown and a further spunbonded layers. The top layer and the bottom layer may be provided from two or more separate sheets of materials or they may be alternatively provided from a unitary sheet of material. Such a unitary sheet of material may be wrapped around the storage layer, e.g., in a C-fold.

Exemplary absorbent structures for use as the absorbent assemblies are described in U.S. Pat. No. 4,834,735, entitled "High Density Absorbent Members Having Lower Density and Lower Basis Weight Acquisition Zones", issued to Alemany et al. on May 30, 1989; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997.

The diaper may also include such other features as are known in the art including front and rear ear panels, waist cap features, elastics and the like to provide better fit, containment and aesthetic characteristics. Such additional features are well known in the art and are described in U.S. Pat. No. 3,860,003 entitled "Contractable side portions for disposable diaper" issued to Buell et al. on Jan. 14, 1975 and U.S. Pat. No. 5,151,092 entitled "Absorbent article with dynamic elastic waist feature having a predisposed resilient flexural hinge" issued to Buell et al. on Sep. 29, 1992.

In order to keep the diaper in place about the wearer, the waist regions and may include a fastening system comprising fastening members preferably attached to the rear waist region. In a preferred embodiment the fastening system further comprises a landing zone attached to the front waist region. The fastening member is attached to the front waist region, preferably to the landing zone to form leg openings and an article waist.

Diapers according to the present invention may be provided with a re-closable fastening system or may alternatively be provided in the form of pant-type diapers. The fastening system and any component thereof may include any material suitable for such a use, including but not limited to plastics, films, foams, nonwoven webs, woven webs, paper, laminates, fiber reinforced plastics and the like, or combinations thereof. It may be preferable that the materials making up the fastening device be flexible. The flexibility is designed to allow the fastening system to conform to the shape of the body and thus, reduces the likelihood that the fastening system will irritate or injure the wearer's skin.

According to one embodiment of the present invention, the topsheet and/or the upper core wrap layer and/or the lower core wrap layer of the absorbent article are made of nonwoven fabric.

IV. Sanitary Tissue Products

The present invention is equally applicable to all types of consumer paper products such as paper towels, toilet tissue, facial tissue, napkins, and the like.

The fibrous structure product herein comprises from about 23% to about 40% of hardwood fibers, such as eucalyptus, tropical hardwood, Acacias, etc., and in another embodiment eucalyptus fibers, wherein the starting hardwood fibers (as measured pre-papermaking) have a Runkel Ratio of from about 6.5 to about 15 and a fiber density of from about 12 to about 35 fibers/gram (in millions).

The Runkel Ratio is a measure of the fiber morphology and the fiber collapse properties, and is measured by the following formula:

$$\text{Runkel Ratio} = \frac{(2t)}{\text{Lumen Diameter}}$$

wherein t is equal to the fiber wall thickness.

In one embodiment the hardwood fibers used herein have a Runkel Ratio of about 6.5 to about 15; in another embodiment from about 7 to about 12, and in yet another embodiment from about 7.5 to about 11.

In one embodiment the hardwood fibers used herein have a fiber density of from about 12 to about 35 fibers/gram (in millions); in another embodiment from about 13 to about 30, and in yet another embodiment from about 15 to about 25.

In one embodiment the hardwood fibers used herein comprise from about 10% to about 40%, or about 23% to about 40% of hardwood fibers, such as eucalyptus, in another embodiment from about 27% to about 35%, in yet another embodiment from about 29% to about 33%, of hardwood fibers, by weight of the fibrous structure product.

In one embodiment the fibrous structure product comprises either no or only a low levels of Southern Softwood Kraft (SSK), in another embodiment from about 0.05% to about 10%, in another embodiment from about 0.1% to about 5%, in another embodiment is essentially free of SSK.

In one embodiment the cellulose fibers of the fibrous structure product comprise only NSK and eucalyptus fibers.

In addition to hardwood or specifically eucalyptus fibers, the present invention contemplates the use of a variety of paper making fibers, such as, natural fibers, synthetic fibers, as well as any other suitable fibers, starches, and combinations thereof. Paper making fibers useful in the present invention include cellulosic fibers commonly known as wood pulp fibers. Applicable wood pulps include chemical pulps, such as Kraft, sulfite and sulfate pulps, as well as mechanical pulps including, groundwood, thermomechanical pulp, chemically modified, and the like. Chemical pulps may be used in tissue towel embodiments since they are known to those of skill in the art to impart a superior tactical sense of softness to tissue sheets made therefrom. Pulps derived from deciduous trees (hardwood) and/or coniferous trees (softwood) can be utilized herein. Such hardwood and softwood fibers can be blended or deposited in layers to provide a stratified web. Exemplary layering embodiments and processes of layering are disclosed in U.S. Pat. Nos. 3,994,771 and 4,300,981. Additionally, fibers derived from wood pulp such as cotton linters, bagesse, and the like, can be used. Additionally, fibers derived from recycled paper, which may contain any of all of the categories as well as other non-fibrous materials such as fillers and adhesives used to manufacture the original paper product may be used in the present web. In addition, fibers and/or filaments made from polymers, specifically hydroxyl polymers, may be used in the present invention. Non-limiting examples of suitable hydroxyl polymers include polyvinyl alcohol, starch, starch derivatives, chitosan, chitosan derivatives, cellulose derivatives, gums, arabinans, galactans, and combinations thereof. Additionally, other synthetic fibers such as rayon, polyethylene, and polypropylene fibers can be used within the scope of the present invention. Further, such fibers may be latex bonded.

In one embodiment the paper is produced by forming a predominantly aqueous slurry comprising about 95% to about 99.9% water.

In one embodiment the non-aqueous component of the slurry, used to make the fibrous structure, comprises only eucalyptus and Northern Softwood Kraft. The aqueous slurry is to be pumped to the headbox of the papermaking process.

In addition to the limitations disclosed herein, the fibrous structure product may comprise any tissue-towel paper product known in the industry. Embodiment of these substrates may be made according U.S. Pat No. 4,191,609 issued Mar. 4, 1980 to Trokhan; U.S. Pat. No. 4,300,981 issued to Carstens on Nov. 17, 1981; U.S. Pat. No. 4,191,609 issued to Trokhan on Mar. 4, 1980; U.S. Pat. No. 4,514,345 issued to Johnson et al. on Apr. 30, 1985; U.S. Pat. No.

4,528,239 issued to Trokhan on Jul. 9, 1985; U.S. Pat. No. 4,529,480 issued to Trokhan on Jul. 16, 1985; U.S. Pat. No. 4,637,859 issued to Trokhan on Jan. 20, 1987; U.S. Pat. No. 5,245,025 issued to Trokhan et al. on Sep. 14, 1993; U.S. Pat. No. 5,275,700 issued to Trokhan on Jan. 4, 1994; U.S. Pat. No. 5,328,565 issued to Rasch et al. on Jul. 12, 1994; U.S. Pat. No. 5,334,289 issued to Trokhan et al. on Aug. 2, 1994; U.S. Pat. No. 5,364,504 issued to Smurkowski et al. on Nov. 15, 1995; U.S. Pat. No. 5,527,428 issued to Trokhan et al. on Jun. 18, 1996; U.S. Pat. No. 5,556,509 issued to Trokhan et al. on Sep. 17, 1996; U.S. Pat. No. 5,628,876 issued to Ayers et al. on May 13, 1997; U.S. Pat. No. 5,629,052 issued to Trokhan et al. on May 13, 1997; U.S. Pat. No. 5,637,194 issued to Ampulski et al. on Jun. 10, 1997; U.S. Pat. No. 5,411,636 issued to Hermans et al. on May 2, 1995; EP 677612 published in the name of Wendt et al. on Oct. 18, 1995, and U.S. Patent Application 2004/0192136A1 published in the name of Gusky et al. on Sep. 30, 2004.

The tissue-towel substrates may be manufactured via a wet-laid making process where the resulting web is through-air-dried or conventionally dried. Optionally, the substrate may be foreshortened by creping or by wet microcontraction. Creping and/or wet microcontraction are disclosed in commonly assigned U.S. Pat. No. 6,048,938 issued to Neal et al. on Apr. 11, 2000; U.S. Pat. No. 5,942,085 issued to Neal et al. on Aug. 24, 1999; U.S. Pat. No. 5,865,950 issued to Vinson et al. on Feb. 2, 1999; U.S. Pat. No. 4,440,597 issued to Wells et al. on Apr. 3, 1984; U.S. Pat. No. 4,191,756 issued to Sawdai on May 4, 1980; and U.S. Pat. No. 6,187,138 issued to Neal et al. on Feb. 13, 2001.

Conventionally pressed tissue paper and methods for making such paper are known in the art, for example U.S. Pat. No. 6,547,928 issued to Barnholtz et al. on Apr. 15, 2003. One suitable tissue paper is pattern densified tissue paper which is characterized by having a relatively high-bulk field of relatively low fiber density and an array of densified zones of relatively high fiber density. The high-bulk field is alternatively characterized as a field of pillow regions. The densified zones are alternatively referred to as knuckle regions. The densified zones may be discretely spaced within the high-bulk field or may be interconnected, either fully or partially, within the high-bulk field. Processes for making pattern densified tissue webs are disclosed in U.S. Pat. No. 3,301,746, issued to Sanford, et al. on Jan. 31, 1967; U.S. Pat. No. 3,974,025, issued to Ayers on Aug. 10, 1976; U.S. Pat. No. 4,191,609, issued to on Mar. 4, 1980; and U.S. Pat. No. 4,637,859, issued to on Jan. 20, 1987; U.S. Pat. No. 3,301,746, issued to Sanford, et al. on Jan. 31, 1967; U.S. Pat. No. 3,821,068, issued to Salvucci, Jr. et al. on May 21, 1974; U.S. Pat. No. 3,974,025, issued to Ayers on Aug. 10, 1976; U.S. Pat. No. 3,573,164, issued to Friedberg, et al. on Mar. 30, 1971; U.S. Pat. No. 3,473,576, issued to Amneus on Oct. 21, 1969; U.S. Pat. No. 4,239,065, issued to Trokhan on Dec. 16, 1980; and U.S. Pat. No. 4,528,239, issued to Trokhan on Jul. 9, 1985.

Uncompacted, non pattern-densified tissue paper structures are also contemplated within the scope of the present invention and are described in U.S. Pat. No. 3,812,000 issued to Joseph L. Salvucci, Jr. et al. on May 21, 1974; and U.S. Pat. No. 4,208,459, issued to Henry E. Becker, et al. on Jun. 17, 1980. Uncreped tissue paper as defined in the art are also contemplated. The techniques to produce uncreped tissue in this manner are taught in the prior art. For example, Wendt, et al. in European Patent Application 0 677 612A2, published Oct. 18, 1995; Hyland, et al. in European Patent Application 0 617 164 A1, published Sep. 28, 1994; and Farrington, et al. in U.S. Pat. No. 5,656,132 issued Aug. 12, 1997.

Uncreped tissue paper, in one embodiment, refers to tissue paper which is non-compressively dried, in one embodiment, by through air drying. Resultant through air dried webs are pattern densified such that zones of relatively high density are dispersed within a high bulk field, including pattern densified tissue wherein zones of relatively high density are continuous and the high bulk field is discrete. The techniques to produce uncreped tissue in this manner are taught in the prior art. For example, Wendt, et. al. in European Patent Application 0 677 612A2, published Oct. 18, 1995; Hyland, et. al. in European Patent Application 0 617 164 A1, published Sep. 28, 1994; and Farrington, et. al. in U.S. Pat. No. 5,656,132 published Aug. 12, 1997.

V. Process for Making Organopolysiloxane Coated Nonwovens or Sanitary Tissue Products The process of the present invention refers to the treatment of a plurality of fibers. If formed into nonwoven fabrics, the plurality of fibers is particularly suitable for absorbent articles. The process is very economical. Furthermore, the process is very fast. It can be run at line speeds of at least 200 m/min, more preferably at least 300 m/min and even more preferably at least 400 m/min.

Suitable techniques to obtain such a surface coating are well known in the art and are described for example in European patent application No. 98116895.8, in WO 97/42356 (Gleason) and in WO96/00548 (Ouellette).

In one aspect, the process for treating a plurality of fibers according to the present invention comprises the following steps:

(a) Providing a plurality of fibers. The fibers can be natural fibers (e.g., wool, silk, cellulose, cotton), man made fibers or synthetic fibers made of resins like polyamide, polypropylene, polyethylenes, polyester or polyamides. The fibers typically have diameters ranging from less than 0.001 mm to more than 0.2 mm.

(b) Providing neat or in solution (e.g., aqueous or non-aqueous) the inventive organopolysiloxane polymer of the present invention.

(c) Contacting the plurality of fibers with the inventive organopolysiloxane polymer. monomers and radical polymerization initiator. The hydrophilic monomers are capable to undergo a radical polymerization process.

To achieve a homogenous application of the polymer on the plurality of fibers, kiss-roll coating or spraying are particularly suitable. Both methods are well known in the art. In kiss-roll coating, the polymer is kept in a suitable bath. A rotating cylinder or any other device suitable for this process, contacts the polymer (or polymer solution) with at least a part of its surface. Thus, the polymer is spread on the surface of the cylinder. The plurality of fibers is brought into contact with the cylinder while the cylinder already has the polymer spread on its surface. In this process, the amount of polymer or polymer solution applied on the plurality of fibers can be controlled easily and it is possible to avoid soaking the plurality of fibers with solution.

Hence, the add-on level of polymer absorbed onto the fiber surface can be controlled, which is difficult in a process, where the plurality of fibers is contacted directly with a bath of polymer or polymer solution. Moreover, the amount of polymer solution necessary for the process can be reduced to a minimum.

Alternatively to the kiss-roll coating, the solution can also be sprayed on the surface of the plurality of fibers. Like the kiss-roll coating, spraying enables low and easily controllable add-on level of aqueous solution, which is preferred in the present invention. It is understood, that the polymer does not have to cover the total surface of the fibers.

If the plurality of fibers provided for the process is not a nonwoven fabric but individual fibers or filaments, these individual fibers or filaments might be formed into a nonwoven fabric. In one embodiment of the invention, the plurality of fibers provided for the process is not a nonwoven fabric but individual fibers or filaments. In this embodiment the individual fibers or filaments might be formed into a nonwoven fabric in a further process step at any point of the process, for example before contacting the plurality of fibers with the polymer solution.

In another embodiment of the invention, the plurality of fibers provided for the process is a nonwoven fabric. Absorbent articles according to the present invention comprise nonwoven fabrics with polymer deposited to the surface of the fibers of the nonwoven fabric.

VI. Organopolysiloxane Polymers

The present invention provides a composition comprising a carrier and a blocky cationic organopolysiloxane having the formula:

$M_w D_x T_y Q_z$ wherein:
M=[SiR$_1$R$_2$R$_3$O$_{1/2}$], [SiR$_1$R$_2$G$_1$O$_{1/2}$], [SiR$_1$G$_1$G$_2$O$_{1/2}$], [SiG$_1$G$_2$G$_3$O$_{1/2}$], or combinations thereof;
D=[SiR$_1$R$_2$O$_{2/2}$], [SiR$_1$G$_1$O$_{2/2}$], [SiG$_1$G$_2$O$_{2/2}$] or combinations thereof;
T=[SiR$_1$O$_{3/2}$], [SiG$_1$O$_{3/2}$] or combinations thereof;
Q=[SiO$_{4/2}$];
w=is an integer from 1 to (2+y+2z);
x=is an integer from 5 to 15,000;
y=is an integer from 0 to 98;
z=is an integer from 0 to 98;
R$_1$, R$_2$ and R$_3$ are each independently selected from the group consisting of H, OH, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, C$_1$-C$_{32}$ alkoxy, C$_1$-C$_{32}$ substituted alkoxy, C$_1$-C$_{32}$ alkylamino, and C$_1$-C$_{32}$ substituted alkylamino;
at least one of M, D, or T incorporates at least one moiety G$_1$, G$_2$ or G$_3$; and G$_1$, G$_2$, and G$_3$ are each independently selected from the formula:

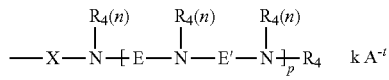

wherein:
X comprises a divalent radical selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide, and ring-opened glycidyl, with the proviso that if X does not comprise a repeating alkylene oxide moiety then X can further comprise a heteroatom selected from the group consisting of P, N and O. Alternatively, each X can be a divalent radical independently selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, and C$_6$-C$_{32}$ substituted arylalkylene;
N=a nitrogen atom;
R$_4$ comprises identical or different monovalent radicals selected from the group consisting of H, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, and C$_6$-C$_{32}$ substituted alkylaryl;

E comprises a divalent radical selected from the group consisting of C$_1$-C$_{32}$ alkylene or C$_3$-C$_{32}$ alkylene, C$_1$-C$_{32}$ substituted alkylene or C$_3$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy or C$_3$-C$_{32}$ alkoxy, C$_1$-C$_{32}$ substituted alkoxy or C$_3$-C$_{32}$ substituted alkoxy, C$_1$-C$_{32}$ alkyleneamino or C$_3$-C$_{32}$ alkyleneamino, C$_1$-C$_{32}$ substituted alkyleneamino or C$_3$-C$_{32}$ substituted alkyleneamino, ring-opened epoxide and ring-opened glycidyl, with the proviso that if E does not comprise a repeating alkylene oxide moiety then E can further comprise a heteroatom selected from the group consisting of P, N, and O;

E' comprises a divalent radical selected from the group consisting of C$_1$-C$_{32}$ alkylene or C$_3$-C$_{32}$ alkylene, C$_1$-C$_{32}$ substituted alkylene or C$_3$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy or C$_3$-C$_{32}$ alkoxy, C$_1$-C$_{32}$ substituted alkoxy or C$_3$-C$_{32}$ substituted alkoxy, C$_1$-C$_{32}$ alkyleneamino or C$_3$-C$_{32}$ alkyleneamino, C$_1$-C$_{32}$ substituted alkyleneamino or C$_3$-C$_{32}$ substituted alkyleneamino, ring-opened epoxide and ring-opened glycidyl, with the proviso that if E' does not comprise a repeating alkylene oxide moiety then E' can further comprise a heteroatom selected from the group consisting of P, N, and O;

In one embodiment, there are no E moieties that are ethylene moieties. Each E and E' can be an identical or different radicals. In some embodiments, E and E' are different radicals.

In some embodiments, at least one E or E' is independently selected from the group consisting of:

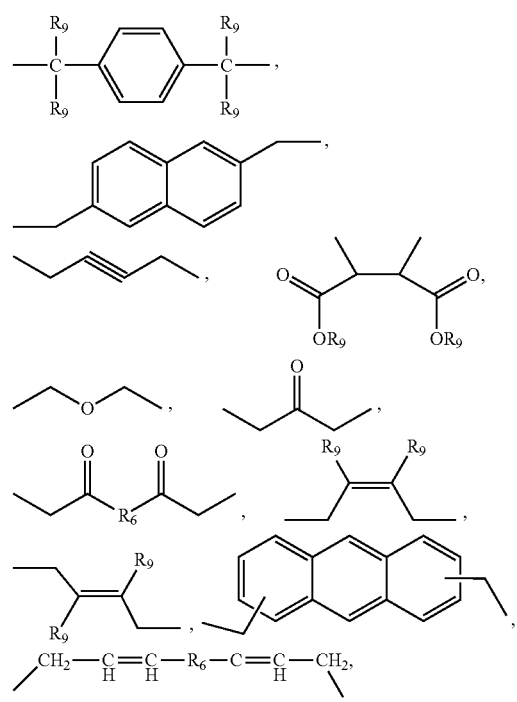

-continued

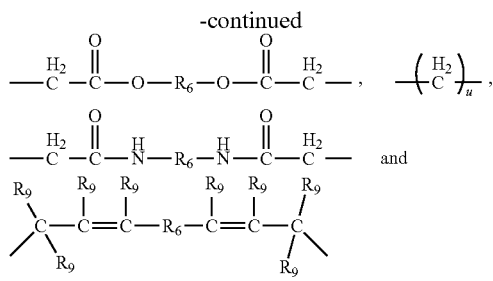

wherein:

R$_6$ comprises a divalent radical selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide, and ring-opened glycidyl, with the proviso that if R$_6$ does not comprise a repeating alkylene oxide moiety then R$_6$ can further comprise a heteroatom selected from the group consisting of P, N, and O;

R$_9$ comprises identical or different monovalent radicals selected from the group consisting of H, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, and C$_6$-C$_{32}$ substituted alkylaryl; and u is an integer independently selected from 3 to 32.

One or more E or E' radical can be an ethylene radical, so long as at least one E or E'radical in the organopolysiloxane polymer is a radical with 3 or more carbon atoms.

Each R$_4$ can be different radicals, and in some embodiments at least one R$_4$ is a methyl radical. In one embodiment R$_4$ is a methyl group or a hydrogen.

p is an integer independently selected from 2 to 100;

n is an integer independently selected from 1 or 2;

when at least one of G$_1$, G$_2$, or G$_3$ is positively charged, A$^{-t}$ is a suitable charge balancing anion or anions such that the total charge, k, of the charge-balancing anion or anions is equal to and opposite from the net charge on the moiety G$_1$, G$_2$ or G$_3$;

where t is an integer independently selected from 1, 2, or 3; and k≤p*2/t+1 such that the total number of cationic charges balances the total number of anionic charges in the organopolysiloxane molecule. A$^{-t}$ can be selected from the group consisting of Cl$^-$, Br$^-$, I$^-$, methylsulfate, toluene sulfonate, carboxylate, phosphate, hydroxide, acetate, formate, carbonate, nitrate, and combinations thereof; or alternatively from the group consisting of Cl$^-$, Br$^-$, I$^-$, methylsulfate, toluene sulfonate, carboxylate, phosphate and combinations thereof.

The organopolysiloxane can have a charge density of from 0.04 meq/g to 12 meq/g, or from 0.04 meq/g to 4 meq/g; or from 1 meq/g to 12 meq/g. In some embodiments, w is an integer from 2 to 50, and in others w is equal to 2. In particular embodiments, x is an integer from 10 to 4,000, or from 40 to 2,000. In one embodiment, w is equal to 2, x is an integer from 20 to 1,000, and y and z are 0.

In one embodiment, G$_1$, G$_2$ and G$_3$ are identical; in another embodiment, G$_1$ and G$_2$ are the same while G$_3$ is different; and in another embodiment, each of G$_1$, G$_2$, and G$_3$ are different. For at least one of G$_1$, G$_2$ or G$_3$, m can be an integer independently selected from 2 to 50, or from 2 to 25, or from 2 to 10. Or, for at least one of G$_1$, G$_2$ or G$_3$, k can be an integer independently selected from 0 to 101, or from 2 to 50. In at least one embodiment, y=z=0. In some embodiments, from 50% to 100% of the amines present in the molecule can be quaternized, or from 70% to 100%, or from 90% to 100%.

One skilled in the art will recognize that the blocky organopolysiloxane of the present invention encompasses a plethora of different embodiments. To this end, when both y and z equal zero, the blocky organopolysiloxane of the present invention can be represented by the formula:

$$M_w D_x$$

where:
M=[SiR$_1$R$_2$R$_3$O$_{1/2}$], [SiR$_1$R$_2$G$_1$O$_{1/2}$], [SiR$_1$G$_1$G$_2$O$_{1/2}$], [SiG$_1$G$_2$G$_3$O$_{1/2}$], or combinations thereof;
D=[SiR$_1$R$_2$O$_{2/2}$];
w=is an integer from 1 to 2;
x=is an integer from 5 to 15,000;
R$_1$, R$_2$ and R$_3$ are each independently selected from the group consisting of H, OH, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, C$_1$-C$_{32}$ alkoxy, C$_1$-C$_{32}$ substituted alkoxy, C$_1$-C$_{32}$ alkylamino, and C$_1$-C$_{32}$ substituted alkylamino;
at least one of M or D incorporates at least one moiety G$_1$, G$_2$ or G$_3$, and G$_1$, G$_2$, and G$_3$ are each independently selected from:

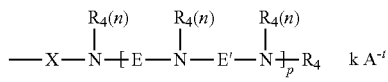

wherein:

X comprises a divalent radical selected from the group consisting of C$_1$-C$_{32}$ alkylene, C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide and ring-opened glycidyl, with the proviso that if X does not comprise a repeating alkylene oxide moiety then X can further comprise a heteroatom selected from the group consisting of P, N, and O. Alternatively, each X can be a divalent radical independently selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, and C$_6$-C$_{32}$ substituted arylalkylene;

R$_4$ comprises identical or different monovalent radicals selected from the group consisting of H, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, and C$_6$-C$_{32}$ substituted alkylaryl;

E comprises a divalent radical selected from the group consisting of C$_1$-C$_{32}$ alkylene or C$_3$-C$_{32}$ alkylene, C$_1$-C$_{32}$ substituted alkylene or C$_3$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy or C$_3$-C$_{32}$ alkoxy, C$_1$-C$_{32}$ substituted alkoxy or C$_3$-C$_{32}$ substituted alkoxy, C$_1$-C$_{32}$ alkyleneamino or C$_3$-C$_{32}$ alkyleneamino, C$_1$-C$_{32}$ substituted alkyleneamino or C$_3$-C$_{32}$ substituted alkyleneamino, ring-opened epoxide and ring-opened glycidyl, with the proviso that if E does not comprise a repeating alkylene oxide moiety then E can further comprise a heteroatom selected from the group consisting of P, N, and O;

E' comprises a divalent radical selected from the group consisting of C$_1$-C$_{32}$ alkylene or C$_3$-C$_{32}$ alkylene, C$_1$-C$_{32}$ substituted alkylene or $C_3$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy or $C_3$-$C_{32}$ alkoxy, $C_1$-$C_{32}$ substituted alkoxy or $C_3$-$C_{32}$ substituted alkoxy, $C_1$-$C_{32}$ alkyleneamino or $C_3$-$C_{32}$ alkyleneamino, $C_1$-$C_{32}$ substituted alkyleneamino or $C_3$-$C_{32}$ substituted alkyleneamino, ring-opened epoxide and ring-opened glycidyl, with the proviso that if E' does not comprise a repeating alkylene oxide moiety then E' can further comprise a heteroatom selected from the group consisting of P, N, and O;

In one embodiment, there are no E moieties that are ethylene moieties. Each E and E' can be an identical or different radicals. In some embodiments, E and E' are different radicals.

In some embodiments, at least one E or E' is independently selected from the group consisting of:

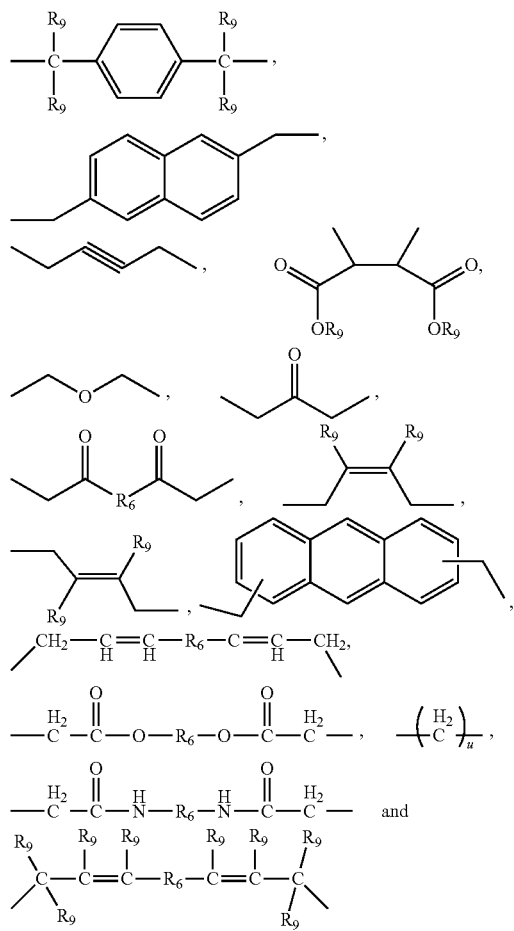

wherein:

$R_6$ comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if $R_6$ does not comprise a repeating alkylene oxide moiety then $R_6$ can further comprise a heteroatom selected from the group consisting of P, N, and O;

$R_9$ comprises identical or different monovalent radicals selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl; and u is an integer independently selected from 3 to 32.

One or more E or E' radical can be an ethylene radical, so long as at least one E or E' radical in the organopolysiloxane polymer is a radical with 3 or more carbon atoms.

Each $R_4$ can be different radicals, and in some embodiments at least one $R_4$ is a methyl radical. In one embodiment $R_4$ is a methyl group or a hydrogen.

p is an integer independently selected from 2 to 100;
n is an integer independently selected from 1 or 2;
when at least one of $G_1$, $G_2$, or $G_3$ is positively charged, $A^{-t}$ is a suitable charge balancing anion or anions such that the total charge, k, of the charge-balancing anion or anions is equal to and opposite from the net charge on the moiety $G_1$, $G_2$ or $G_3$;

where t is an integer independently selected from 1, 2, or 3; and $k \leq (p*2/t)+1$ such that the total number of cationic charges balances the total number of anionic charges in the organopolysiloxane molecule. $A^{-t}$ can be selected from the group consisting of $Cl^-$, $Br^-$, $I^-$, methylsulfate, toluene sulfonate, carboxylate, phosphate, hydroxide, acetate, formate, carbonate, nitrate, and combinations thereof; or alternatively from the group consisting of $Cl^-$, $Br^-$, $I^-$, methylsulfate, toluene sulfonate, carboxylate, phosphate and combinations thereof.

In one embodiment, E or E' is a primary alkyl chain having 3 or more carbon atoms, or 4 or more carbon atoms, or 5 or more carbon atoms, or from 4 to 32 carbon atoms. Without being limited by theory, it is believed that in embodiments where E or E' is a primary alkyl chain having exactly 2 carbon atoms, the moiety G can be unstable relative to the potential for an elimination reaction. This is because an undesirable elimination reaction is likely to take place, due to an unshared electron pair reacting to create an alkene.

In another embodiment, the moiety E or E' can be independently selected from different groups of different length to control the spacing and density of the charges along the chain. In certain applications, it can be desirable to have these charges closely spaced, and in other applications it can be desirable to have these charges spaced farther apart. The charged moiety G can be separate from the silicone portion of the organopolysiloxane, and more specifically, disposed at the terminal ends of the siloxane moiety. Without being bound by theory, it is believed that maintaining the charges in a "blocky" fashion disposed at the ends of a terminal siloxane moiety, allows the siloxane moiety to project further out from the surface of the treated substrate, resulting in a more lubricious, softer feel for the treated substrate.

In one aspect, the carrier is selected from water, surfactants, solvents, emulsifiers, and mixtures thereof.

EXAMPLES

Exemplary organopolysiloxanes of the present invention were formulated into the following emulsion was prepared for application to nonwovens for use in the consumer products set forth herein. The organopolysiloxanes from Example 1 below were used to make the emulsions and were applied to nonwovens in making the examples below.

In the nonlimiting example herein, the organopolysiloxane was emulsified in an aqueous carrier prior to being applied to the nonwoven or sanitary tissue product. It can be appreciated by one of ordinary skill in the art that any of a number of means of applying the organopolysiloxane to the nonwoven can be utilized. The organopolysiloxane may be emulsified prior to application to the nonwoven or sanitary tissue product, including emulsification into water or other primarily aqueous carrier. The organopolysiloxane may be dissolved in a suitable carrier prior to application to the nonwoven. The carrier may be volatile to facilitate removal of the carrier after treatment of the nonwoven or sanitary tissue product.

The materials in Table 1 were used to make 20% active emulsions of the polyorganosiloxane for application to the nonwovens of the present invention. The materials of Table 2 were first emulsified using a homogenizer at 3,500 rpm, and then microfluidized at 20,000 psi to obtain a less than 5 micron particle size emulsions.

TABLE 1

| Ex. | x | $R_3$ | E | E' | m | $A^{-t}$ | k | Charge Density (meq/g of polymer) |
|---|---|---|---|---|---|---|---|---|
| 1 | 400 | NA | Hexylene | hexylene | 10 | $Br^-$ | 11 | 0.64 |

TABLE 2

| Material | % |
|---|---|
| Organopolysiloxane of Example 1 | 20.00 |
| Tergitol 15-S-5[1] | 3.00 |
| Acetic Acid | 0.60 |
| Dilution Water | q.s to 100% |

[1]Available from Sigma Aldrich

In one non-limiting example of the present invention, the organopolysiloxane of Example 1 was emulsified as described above and applied to a 24 gsm polypropylene soft bound bico non-woven known in the art as a top sheet for a disposible absorbent article. The emulsion was air sprayed onto the non-woven top sheet to obtain a final coating of 5 gsm of the emulsion. The top sheet was air dried over night to yield a total of 1 gsm of the organopolysiloxane of Example 1. The treated nonwoven top sheet was left to equilibrate in a controlled humidity room prior to further evaluation.

In another non-limiting example of the present invention, the organopolysiloxane of Example 1 was emulsified as described above and applied to a 17 gsm polypropylene spunbound non-woven known in the art as a top sheet for a disposable absorbent article. The emulsion was air sprayed onto the non-woven top sheet to obtain a final coating of 4 gsm of the emulsion. The top sheet was air dried over night to yield a total of 0.8 gsm of the organopolysiloxane Example 1. The treated nonwoven top sheet was left to equilibrate in a controlled humidity room prior to further evaluation.

Softening benefits of these molecules on substrates (top sheets and paper) were evaluated using an Instron friction measurement (IFM) method, though it will be understood by one of ordinary skill in the art that friction can be assessed by any of a number of means.

Nonwoven softness was evaluated by an Instron friction measurement (IFM). In the method, a 200 g sled-weight is put on the middle of a sample of the nonwoven and the force required to slide the nonwoven bearing the 200 g sled-weight is recorded with a lower force to slide indicating a more lubricious and softer material. The bottom of the sled is prepared by attaching a piece of polyurethane that exactly fits the bottom of the sled including edges. The measurement is performed five times per treatment averaged. Treated nonwovens were compared to identical untreated nonwovens in demonstrating the softness benefit.

Example 2

24 gsm Polypropylene Soft Bound Bico Nonwoven Top-sheet

| Sample Name | Coefficient of Friction (gF) |
|---|---|
| Nonwoven treated with 1 gsm of organopolysiloxane of Example 1 | 279 |
| Untreated Nonwoven | 360 |

Example 3

17 gsm Polypropylene Spunbound NonWoven Top-sheet

| Sample Name | Coefficient of Friction (gF) |
|---|---|
| Nonwoven treated with 0.8 gsm of organopolysiloxane of Example 1 | 64 |
| Untreated Nonwoven | 105 |

In another non-limiting example of the present invention, the organopolysiloxane of Example 1 was emulsified as described above and applied to a bathroom toilet tissue. The emulsion was applied using a kiss-roll onto the toilet tissue to obtain a final coating of 3750 ppm of the organopolysiloxane polymer after dried.

What is claimed is:

1. A disposable absorbent article comprising a topsheet, a backsheet, and an absorbent core disposed between said topsheet and said backsheet, wherein said topsheet comprises a nonwoven fabric coated with a blocky cationic organopolysiloxane having the formula:

$$M_w D_x T_y Q_z$$

wherein:
M=[SiR$_1$R$_2$R$_3$ O$_{1/2}$], [SiR$_1$R$_2$G$_1$O$_{1/2}$], [SiR$_1$G$_1$G$_2$O$_{1/2}$ ], [SiG$_1$G$_2$G$_3$O$_{1/2}$ ], or combinations thereof;
D=[SiR$_1$R$_2$O$_{2/2}$], [SiR$_1$G$_1$O$_{2/2}$], [SiG$_1$G$_2$O$_{2/2}$] or combinations thereof;
T=[SiR$_1$O$_{3/2}$], [SiG$_1$O$_{3/2}$] or combinations thereof;
Q=[SiO$_{4/2}$];
w=is an integer from 1 to (2+y+2z);
x=is an integer from 5 to 15,000;
y=is an integer from 0 to 98;
z=is an integer from 0 to 98;
R$_1$, R$_2$ and R$_3$ are each independently selected from the group consisting of H, OH, C$_1$-C$_{32}$ alkyl, C$_1$-C$_{32}$ substituted alkyl, C$_5$-C$_{32}$ aryl, C$_5$-C$_{32}$ substituted aryl, C$_6$-C$_{32}$ alkylaryl, C$_6$-C$_{32}$ substituted alkylaryl, C$_1$-C$_{32}$ alkoxy, C$_1$-C$_{32}$ substituted alkoxy, C$_1$-C$_{32}$ alkylamino, and C$_1$-C$_{32}$ substituted alkylamino;
at least one of M, D, or T incorporates at least one moiety G$_1$, G$_2$ or G$_3$; and $G_1$, $G_2$, and $G_3$ are identical or different moieties, each of which has the formula:

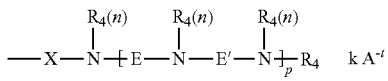

wherein:
X comprises a divalent radical selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if X does not comprise a repeating alkylene oxide moiety then X can further comprise a heteroatom selected from the group consisting of P, N and O;
each $R_4$ comprises identical or different monovalent radicals independently selected from the group consisting of H, $C_1$-$C_{32}$ alkyl, $C_1$-$C_{32}$ substituted alkyl, $C_5$-$C_{32}$ aryl, $C_5$-$C_{32}$ substituted aryl, $C_6$-$C_{32}$ alkylaryl, and $C_6$-$C_{32}$ substituted alkylaryl;
E comprises a divalent radical selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide and ring-opened glycidyl, with the proviso that if E does not comprise a repeating alkylene oxide moiety then E can further comprise a heteroatom selected from the group consisting of P, N, and O;
E' comprises a divalent radical selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide and ring-opened glycidyl, with the proviso that if E' does not comprise a repeating alkylene oxide moiety then E' can further comprise a heteroatom selected from the group consisting of P, N, and O;
p is an integer independently selected from 1 to 50;
n is an integer independently selected from 1 or 2;
when at least one of $G_1$, $G_2$, or $G_3$ is positively charged, $A^{-t}$ is a suitable charge balancing anion or anions such that the total charge, k, of the charge-balancing anion or anions is equal to and opposite from the net charge on the moiety $G_1$, $G_2$ or $G_3$; where t is an integer independently selected from 1, 2, or 3; and wherein k $\leq$p*2/t+1, for each moiety G.

2. The article according to claim 1, wherein each E of the organopolysiloxane comprises a divalent radical selected from the group consisting of $C_3$-$C_{32}$ alkylene, $C_3$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_3$-$C_{32}$ alkoxy, $C_3$-$C_{32}$ substituted alkoxy, $C_3$-$C_{32}$ alkyleneamino, $C_3$-$C_{32}$ substituted alkyleneamino, ring-opened epoxide, and ring-opened glycidyl, with the proviso that if E does not comprise a repeating alkylene oxide moiety then E can further comprise a heteroatom selected from the group consisting of P, N, and O; and wherein E' of the organopolysiloxane comprises a divalent radical selected from the group consisting of $C_3$-$C_{32}$ alkylene, $C_3$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_3$-$C_{32}$ alkoxy, $C_3$-$C_{32}$ substituted alkoxy, $C_3$-$C_{32}$ alkyleneamino, $C_3$-$C_{32}$ substituted alkyleneamino, ring-opened epoxide, and ring-opened glycidyl, with the proviso that if E' does not comprise a repeating alkylene oxide moiety then E' can further comprise a heteroatom selected from the group consisting of P, N, and O.

3. A disposable absorbent article comprising a topsheet, a backsheet, and an absorbent core disposed between said topsheet and said backsheet, wherein said topsheet comprises a nonwoven fabric coated with a blocky organopolysiloxane having the formula:

$$M_w D_x$$

where:
$M=[SiR_1R_2R_3O_{1/2}]$, $[SiR_1R_2G_1O_{1/2}]$, $[SiR_1G_1G_2O_{1/2}]$, $[SiG_1G_2G_3O_{1/2}]$, or combinations thereof;
$D=[SiR_1R_2O_{2/2}]$;
w=is an integer from 1 to 2;
x=is an integer from 5 to 15,000;
$R_1$, $R_2$ and $R_3$ are each independently selected from the group consisting of H, OH, $C_1$-$C_{32}$ alkyl, $C_1$-$C_{32}$ substituted alkyl, $C_5$-$C_{32}$ aryl, $C_5$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy, $C_1$-$C_{32}$ alkylamino, and $C_1$-$C_{32}$ substituted alkylamino;
at least one of M or D incorporates at least one moiety $G_1$, $G_2$ or $G_3$, and $G_1$, $G_2$, and $G_3$ are identical or different moieties each of which has the formula:

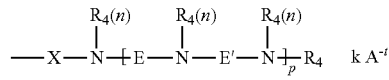

wherein:
X comprises a divalent radical selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide and ring-opened glycidyl, with the proviso that if X does not comprise a repeating alkylene oxide moiety then X can further comprise a heteroatom selected from the group consisting of P, N, and O;
$R_4$ comprises identical or different monovalent radicals selected from the group consisting of H, $C_1$-$C_{32}$ alkyl, $C_1$-$C_{32}$ substituted alkyl, $C_5$-$C_{32}$ aryl, $C_5$-$C_{32}$ substituted aryl, $C_6$-$C_{32}$ alkylaryl, and $C_6$-$C_{32}$ substituted alkylaryl;
E comprises a divalent radical selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if E does not comprise a repeating alkylene oxide moiety then E can further comprise a heteroatom selected from the group consisting of P, N, and O;
E' comprises a divalent radical selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if E' does not comprise a repeating alkylene oxide moiety then E' can further comprise a heteroatom selected from the group consisting of P, N, and O;

p is an integer independently selected from 1 to 50;

n is an integer independently selected from 1 or 2; and when at least one of $G_1$, $G_2$, or $G_3$ is positively charged, $A^{-t}$ is a suitable charge balancing anion or anions such that the total charge, k, of the charge-balancing anion or anions is equal to and opposite from the net charge on the moiety $G_1$, $G_2$ or $G_3$; wherein t is an integer independently selected from 1, 2, or 3; and wherein k ≤p*2/t+1 for each moiety G.

4. An article according to claim 3 wherein each E in the organopolysiloxane comprises a divalent radical selected from the group consisting of $C_3$-$C_{32}$ alkylene, $C_3$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_3$-$C_{32}$ alkoxy, $C_3$-$C_{32}$ substituted alkoxy, $C_3$-$C_{32}$ alkyleneamino, $C_3$-$C_{32}$ substituted alkyleneamino, ring-opened epoxide, and ring-opened glycidyl, with the proviso that if E does not comprise a repeating alkylene oxide moiety then E can further comprise a heteroatom selected from the group consisting of P, N, and O; and wherein E' in the organopolysiloxane comprises a divalent radical selected from the group consisting of $C_3$-$C_{32}$ alkylene, $C_3$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_3$-$C_{32}$ alkoxy, $C_3$-$C_{32}$ substituted alkoxy, $C_3$-$C_{32}$ alkyleneamino, $C_3$-$C_{32}$ substituted alkyleneamino, ring-opened epoxide, and ring-opened glycidyl, with the proviso that if E' does not comprise a repeating alkylene oxide moiety then E' can further comprise a heteroatom selected from the group consisting of P, N, and O.

5. An article according to claim 1, wherein at least one E or E' of the organopolysiloxane is independently selected from the group consisting of:

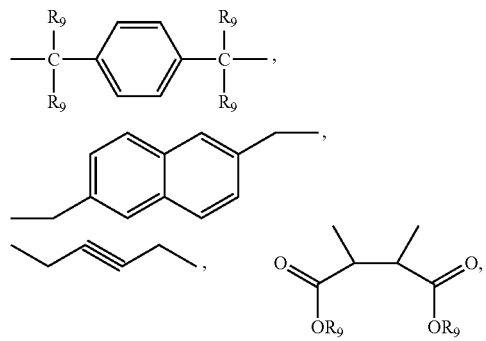

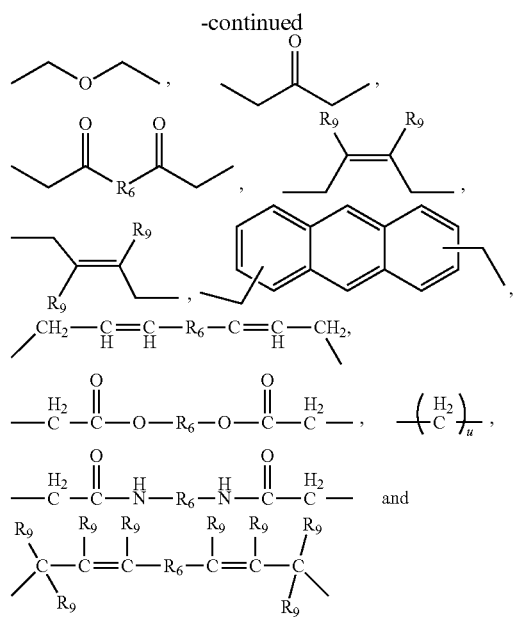

wherein:
each $R_6$ comprises a divalent radical independently selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if $R_6$ does not comprise a repeating alkylene oxide moiety then $R_6$ can further comprise a heteroatom selected from the group consisting of P, N, and O;

each $R_9$ comprises monovalent radicals independently selected from the group consisting of H, $C_1$-$C_{32}$ alkyl, $C_1$-$C_{32}$ substituted alkyl, $C_5$-$C_{32}$ aryl, $C_5$-$C_{32}$ substituted aryl, $C_6$-$C_{32}$ alkylaryl, and $C_6$-$C_{32}$ substituted alkylaryl; and u is an integer independently selected from 3 to 32.

6. The article of claim 1, wherein said disposable absorbent article is selected from the group consisting of baby diapers, training pants, adult incontinence articles, feminine protection articles, bed pads, and incontinent pads.

7. The article of claim 1 comprising less than 1 gram per square meter (gsm), or from 0.01-10 gsm, or from 0.01-5 gsm, or from 0.01-2 gsm of organopolysiloxane after said article is dried.

8. A method of making the disposable absorbent article of claim 1, wherein the organopolysiloxane is blended with a carrier prior to being applied to the nonwoven fabric.

9. The method of claim 8, wherein said carrier is selected from the group consisting of water, ethanol, solvents, isopropanol, surfactant, emulsifier, and combinations thereof.

10. The method of claim 8, wherein the carrier comprises water and the organopolysiloxane is emulsified with the water prior to application to the nonwoven fabric.

* * * * *